United States Patent
Hoffman et al.

(10) Patent No.: US 8,246,559 B2
(45) Date of Patent: Aug. 21, 2012

(54) TWO DEGREE OF FREEDOM POWERED ORTHOSIS

(75) Inventors: Allen H. Hoffman, Sterling, MA (US);
Michael J. Scarsella, Sterling, MA (US); Steven P. Toddes, Gettysburg, PA (US); Daniel N. Abramovich, Chestnut Hill, MA (US)

(73) Assignee: Worcester Polytechnic Institute, Worcester, MA (US)

( * ) Notice: Subject to any disclaimer, the term of this patent is extended or adjusted under 35 U.S.C. 154(b) by 691 days.

(21) Appl. No.: 12/439,555

(22) PCT Filed: Sep. 4, 2007

(86) PCT No.: PCT/US2007/077553
§ 371 (c)(1),
(2), (4) Date: Mar. 2, 2009

(87) PCT Pub. No.: WO2008/028190
PCT Pub. Date: Mar. 6, 2008

(65) Prior Publication Data
US 2009/0326422 A1    Dec. 31, 2009

Related U.S. Application Data

(60) Provisional application No. 60/841,791, filed on Sep. 1, 2006.

(51) Int. Cl.
*A61F 5/37* (2006.01)
*A61F 13/00* (2006.01)
*A61F 5/00* (2006.01)
*A61F 13/06* (2006.01)

(52) U.S. Cl. ............ 602/20; 602/5; 602/16; 602/60; 602/61; 602/62; 128/846; 128/869; 128/878; 128/881

(58) Field of Classification Search ............ 602/5, 16, 602/20, 60–62; 128/846, 869, 878, 881
See application file for complete search history.

(56) References Cited

U.S. PATENT DOCUMENTS

| 5,848,979 | A | 12/1998 | Bonutti et al. |
| 6,113,562 | A * | 9/2000 | Bonutti et al. ............ 602/20 |
| 6,599,263 | B1 * | 7/2003 | Bonutti et al. ............ 602/20 |
| 6,929,616 | B2 * | 8/2005 | Bonutti et al. ............ 602/20 |
| 7,955,285 | B2 * | 6/2011 | Bonutti et al. ............ 602/16 |
| 2004/0106881 | A1 | 6/2004 | McBean et al. |

OTHER PUBLICATIONS

Written Opinion of the International Searching Authority, International Search Report sent Aug. 8, 2008, International Application No. PCT/US07/77553.

\* cited by examiner

*Primary Examiner* — Patricia Bianco
*Assistant Examiner* — Brandon L Jackson
(74) *Attorney, Agent, or Firm* — Burns & Levinson LLP; Jacob N Erlich; David W Gomes

(57) ABSTRACT

Weakened and restricted limb movement is aided by powered orthosis having one or more independent dimensions of controlled movement and a control system.

20 Claims, 10 Drawing Sheets

TWO DEGREE OF FREEDOM POWERED ORTHOSIS

CROSS REFERENCE TO RELATED APPLICATIONS

This application claims priority from U.S. Provisional Patent Application Ser. No. 60/841,791, filed Sep. 1, 2006 and incorporated herein by reference in its entirety.

FIELD OF THE INVENTION

The present invention generally relates to orthotic devices, and in particular to such devices which are motorized to aid limb movement.

BACKGROUND OF THE INVENTION

Rehabilitation engineering aims to improve the quality of life for individuals with varying disabilities. Paraplegia, for example, has seen significant attention from the rehabilitation field, offering several mobility devices, orthoses, and accessories to improve the client's independence. Other disabilities, especially those, which have a variety of forms or progress very quickly, have seen little attention. Muscular Dystrophy (MD) is this type of disability. Muscular dystrophy is a genetic, degenerative disease, which destroys muscle tissue leading to decreased mobility and independence.

Muscular dystrophy is a term used to describe any one of a group of degenerative muscular diseases. MD causes weakness or wasting away of the skeletal muscles. There are over 40 identified neuromuscular diseases. They are hereditary and express themselves in known patterns of inheritance. The diseases are myopathies because they are an inherent disorder of the muscle. They affect all populations with no variation among regions.

Muscular dystrophies are a relatively rare condition. The most prevalent type, Duchenne, occurs in only 30 cases per 100,000 births. It was not until 1987 when scientists discovered the specific DNA alterations and could determine the exact protein that is missing or dysfunctional in patients with the disease. Prior to that date, doctors identified these diseases based on clinical and genetic characteristics. Currently, the differentiation between each type of muscular dystrophy is determined partially based on the pattern of inheritance and the affected muscle group(s).

Duchenne, the most common form of MD is inherited as an X-linked recessive disease. Therefore, this pattern generally affects males. Women are responsible for carrying the gene, but only in very rare cases ever experience any symptoms of the disability. Symptoms typically begin before the age of three with difficulty in walking. By adolescence, patients become confined in wheelchairs. Dexterity in the fingers and wrist remain high through the natural progression of the disease. Eventually DMD affects the respiratory muscles causing death.

A rehabilitation device, which would increase the range of motion of muscle groups, would benefit clients suffering from Duchenne's MD by improving their independence and overall quality of life. Such a product could have influence in the rehabilitation, therapeutic, and medical markets for clients with afflictions other than muscular dystrophy. The potential exists for the product to also aid patients with arm tremor and tendonitis, to rehabilitate those suffering from stroke and arthritis, and to assist in therapy for those recovering from surgery or injury.

The human body is composed of some of the most intricate and ingenious mechanical systems known to man. The arm, specifically, involves a precisely arranged set of muscles and joints, which allows a person to target any object within his/her arm's radius. In total, the arm incorporates seven degrees of freedom (DOF) to complete its specified motions. These DOF occur at joints of the shoulder, elbow, and wrist regions by multiple movements at each joint. The shoulder joint allows the arm to swing forward and backward (forward flexion and backward extension), swing laterally (horizontal flexion and horizontal extension), and swing about an axis through the front of the body (abduction and adduction). The wrist joint allows the hand to swing up and down (flexion and extension) and swing sideways (radial deviation and ulnar deviation). The elbow joint accounts for the remainder of the arm's DOF with its forearm pronation and supination (rotation of the forearm and wrist about an axis through the forearm) and its elbow flexion and extension (a curling motion between the forearm and upper arm).

The skeletal structure 10 of the arms and upper torso is shown in the front and rear views, respectively of FIGS. 1A and 1B. The humerus 11 is the solitary bone in the upper arm's skeletal structure. This bone pivots in three rotational DOF from its proximal end at the shoulder joint 12, the way a rod pivots with its end connected to a socket as a ball joint. The connection of the humerus 11 to the joint occurs at the scapula 13 and the clavicle 14 at the shoulder, and the scapula's glenoid cavity serves as the socket joint in this connection. The motions that this joint allows include the abduction, flexion, and extension as well as humeral rotation. Humeral rotation is associated with the motion of forward flexion and backward extension. As one extends an arm forward, the arm rotates orthogonally about an axis 15 through the side of the shoulder. When the arm abducts to 90 degrees, the person can still make a rotation about the arm by rotating the humerus 11. The DOF of rotation about the arm can be achieved at different positions. The distal end of humerus 11 connects to the elbow joint 16, where it is the base for the flexion and extension of the forearm. The ulna 17 and radius 18 are the two bones that comprise the skeletal structure of the forearm 19. The ulna 17 serves as an axis about which the radius 18 can revolve, in order to produce the pronation and supination of the wrist 20. The proximal end of the forearm 19 attaches to the elbow joint 16, where it acts as a lever with respect to the humerus 11. The distal end of the forearm 19 connects to the hand with an intricate array of muscles, bones, and ligaments.

In view of the above discussion, it would be beneficial to have a powered arm orthosis capable of manipulating a disabled arm in the normal manner of common arm movements such as humeral rotation and elbow flexion.

SUMMARY OF THE INVENTION

In one embodiment, the present invention provides an arm orthosis adapted for providing humeral rotation and elbow flexion to a human arm, comprising: a humeral member adapted for attachment to an upper arm of a person; an elbow assembly adapted for attachment to a forearm of a person; and an attachment mechanism adapted to attach the elbow assembly to the humeral member and to effect rotation of the elbow assembly, in a manner of a human arm, with respect to the humeral member; wherein the elbow assembly includes a flexion mechanism for bending the elbow assembly in a manner of a human elbow.

The attachment mechanism may include an arcuate member attached to the elbow assembly and a translational mechanism engaging the arcuate member and adapted to provide support to the arcuate member and translational movement of the arcuate member with respect to the translational mechanism to provide the rotation of the elbow assembly with respect to the humeral member.

The elbow assembly may further include a pair of elongated members individually and adjustably attached to opposing ends of the arcuate member. The pair of elongated members may each include a matching pivotal point adapted for location on either side of a human elbow of an arm attached to the orthosis. The elbow assembly may include a forearm brace adapted for attachment to a forearm of a person, and a pair of forearm brace axle sections adapted to individually, rotatably interface with a separate one of the pair of elongated members.

The arm orthosis may further comprise a flexion drive attached to one of the elongated members and adapted to rotate the forearm brace with respect to one of the elongated members. The flexion drive may include a drive gear affixed to one of the forearm brace axle sections at a point on that axle section which extends through an elongated member. The flexion drive may include a flexion drive electrical motor and a worm gear located to engage the drive gear. The flexion drive may include a flexion sensor adapted to indicate amounts of rotation between one elongated member and the forearm brace. The flexion sensor may include a mechanical/electrical sensor coupled to sense amounts of rotation of the flexion drive electrical motor.

The arcuate member may include upper and lower bearing surfaces arranged to enable supportive engagement of the arcuate member by the translational mechanism. The arcuate member may include an arcuate gear section located along the arcuate member, and the translational mechanism may include a worm gear and a humeral electric motor adapted to drive the arcuate gear section to cause the translational movement. The translational mechanism may include a humeral sensor adapted to indicate amounts of movement between the arcuate member and the translational mechanism. The humeral sensor may include a mechanical/electrical sensor coupled to sense amounts of rotation of the humeral electrical motor.

The humeral member may be adapted for removable attachment to an upper arm of a person, and the elbow assembly may be adapted for removable attachment to a forearm of a person.

The attachment mechanism and the flexion mechanism may be electrically driven, and the orthosis may further comprise a control system adapted for simultaneously and independently controlling driven movement of the attachment mechanism and the flexion mechanism. The control system may include a joystick control adapted for providing one-handed simultaneous input signals for both the attachment mechanism and the flexion mechanism. The joystick control may be adapted to provide a variable magnitude input signal, and the control system may be adapted to convert the variable magnitude input signal to a variable speed control for the electrically driven attachment mechanism and the flexion mechanism.

The control system may include control circuitry for the attachment mechanism and the flexion mechanism, a controller adapted for receiving user inputs and a wireless link between the controller and the control circuitry. The control circuitry is adapted to receive feedback movement data from the attachment mechanism and the flexion mechanism and to limit drive signals to the attachment mechanism and the flexion mechanism in response to the feedback movement data.

The control system may include a logic controller for translating or interpreting inputs received from input circuitry, including myoelectric sensors.

In another embodiment, the present invention provides a control system for a powered orthosis having one or more independent dimensions of movement, comprising input circuitry adapted for receiving separate control inputs for the one or more dimensions of movement and drive circuitry adapted to provide a separate drive signal for each of the one for more dimensions of movement in response to inputs received by the input circuitry and further adapted to receive and use feedback inputs from an orthosis for limiting drive signals.

The input circuitry may be adapted to encode two directions of movement with magnitudes for each and a neutral position into a continuously variable input signal for each dimension of movement; and the control circuitry may be adapted to use two separate direction and magnitude of movement signals and a separate brake signal for each dimension of movement. The control system may further comprise logic circuitry adapted to convert the continuously variable input signal into the two separate direction and magnitude signals and a separate brake signal. The control system may still further comprise a wireless transmission system between the input circuitry and the logic and control circuitry.

The control system may include a joystick control adapted for providing one-handed simultaneous input signals for both the attachment mechanism and the flexion mechanism. The joystick control may be adapted to provide a variable magnitude input signal, wherein the control system is adapted to convert the variable magnitude input signal to a variable speed control for the electrically driven attachment mechanism and the flexion mechanism.

The control system may further comprise a logic controller for translating or interpreting inputs received by the input circuitry, wherein the input circuitry includes myoelectric sensors.

BRIEF DESCRIPTION OF THE DRAWINGS

The present invention is illustratively shown and described in reference to the accompanying drawings, in which.

DETAILED DESCRIPTION OF THE DRAWINGS

Figure 1B:
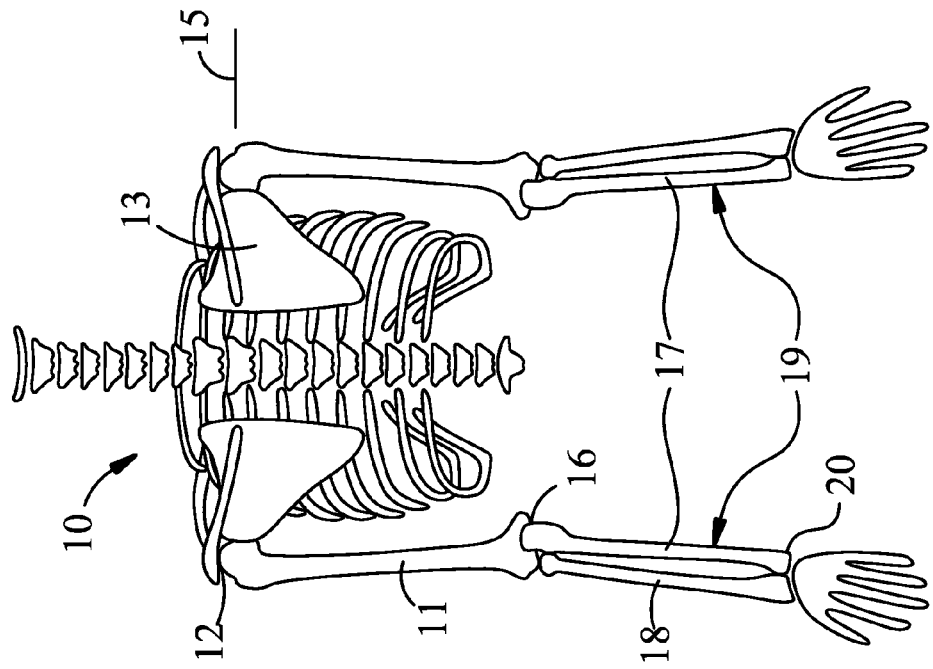
FIGS. 1A and 1B show front and back skeletal diagrams, respectively, of a human chest, arms and neck.
Figure 1A:
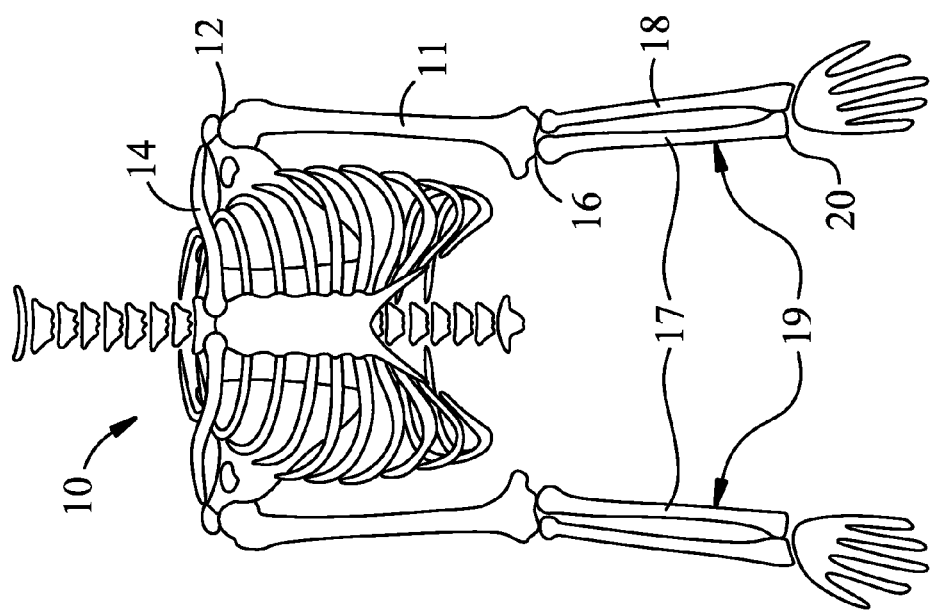
Figure 2:
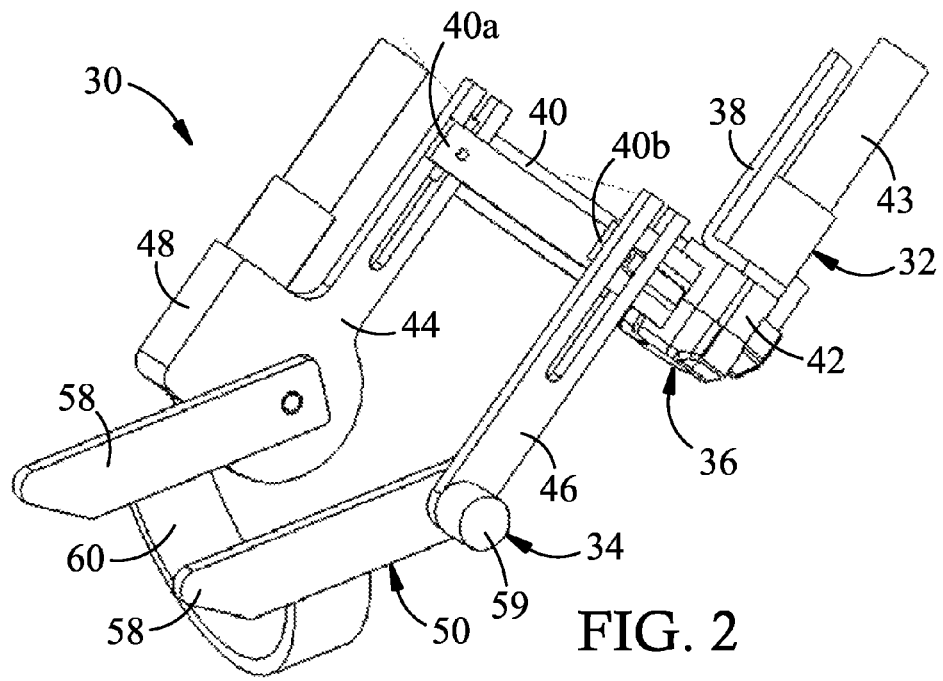
FIG. 2 is a perspective view of a motorized arm orthosis constructed in accordance with one embodiment of the present invention.
Figure 3:
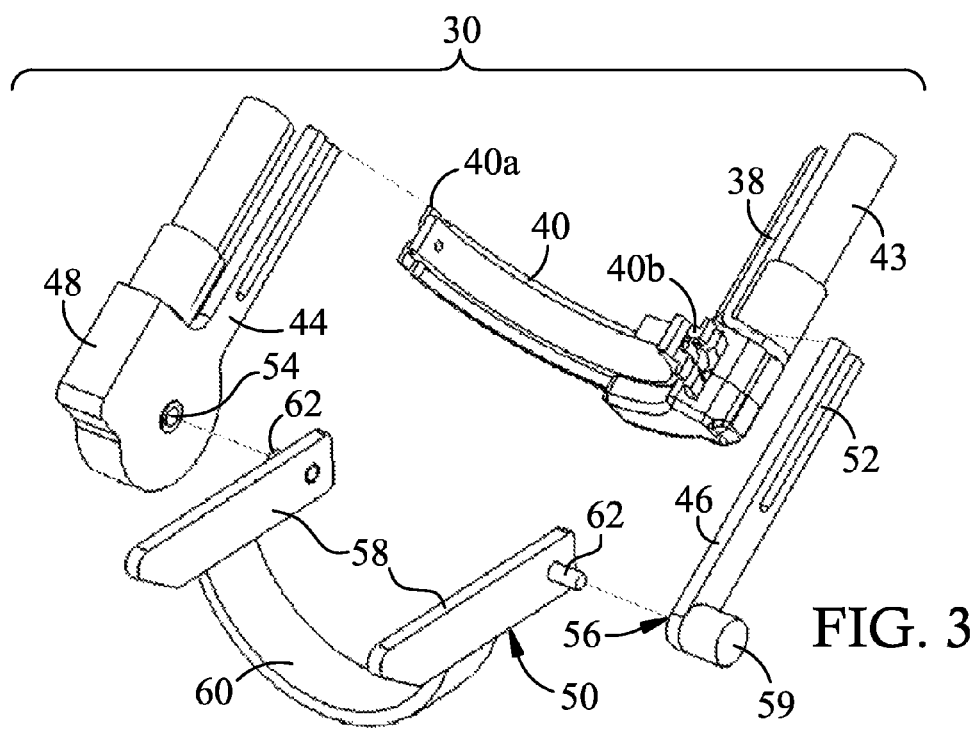
FIG. 3 is a perspective view of the arm orthosis of FIG. 2 having its basic component parts disassembled.

FIGS. 2 and 3 show perspective views of an arm orthosis 30 constructed in accordance with one embodiment of the present invention. FIG. 3 shows an exploded view of the assembled orthosis 30 of FIG. 2. Generally included in orthosis 30 are a humeral member 32, an elbow assembly 34 and an attachment mechanism 36 adapted to attach elbow assembly 34 to humeral member 32.

Humeral member 32 includes an arm attachment member 38 which may be suitably strapped to an upper arm area of a wearer of orthosis 30. Attachment mechanism 36 is integrally constructed with humeral member 32 and generally includes an arcuate member 40, a translational mechanism 42 coupled to an electric humeral motor 43.

Elbow assembly 34 generally includes a pair of elongated members 44, 46, a flexion mechanism 48 and a forearm brace 50. The elongated members 44, 46 are adapted to be individually and adjustably attached to separate opposing ends 40a, 40b, respectively, of arcuate member 40. Elongated members 44, 46 each includes an elongated slot 52 formed to enable this adjustable attachment in a manner which suitably supports elbow assembly 34 from arcuate member 40. Elongated members 44, 46 are further adapted to be oriented parallel to each other and to the upper arm of a wearer of orthosis 30, and further, each includes a matching pivotal point 54, 56, respectively, adapted for location on either side of a human elbow of a wearer's arm. Forearm brace 50 is adapted for attachment to a human forearm by any suitable strap arrangement as described below in reference to FIG. 13, and includes a pair of bilateral members 58 interconnected by a peripheral member 60 adapted to curve beneath a wearer's arm. Bilateral members 58 each includes an axle section 62 adapted to individually, rotatably interface with a separate one of the pair of elongated members 44, 46 at their respective pivotal points 54, 56. Elbow assembly 34 may further include a mechanical position sensor 59, such as a potentiometer, which senses the relative position between elongated member 46 and forearm brace 50 via an axle section 62. This can provide position feedback to a control system as described below.

Figure 4:
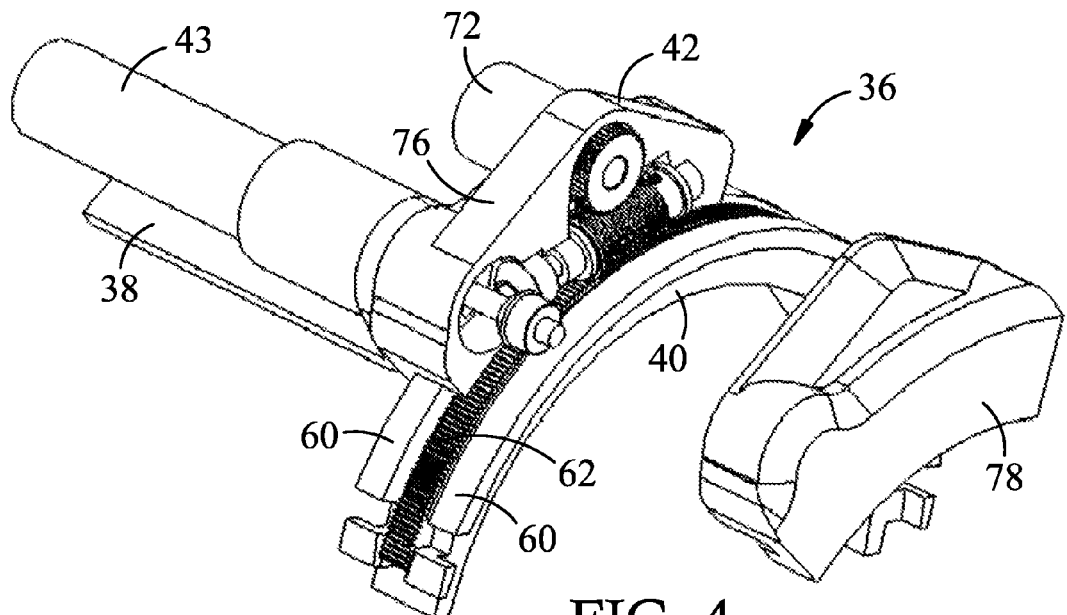
FIG. 4 is a perspective view of a portion of the orthosis of FIGS. 2 and 3 opened to expose some internal mechanism.
Figure 5:
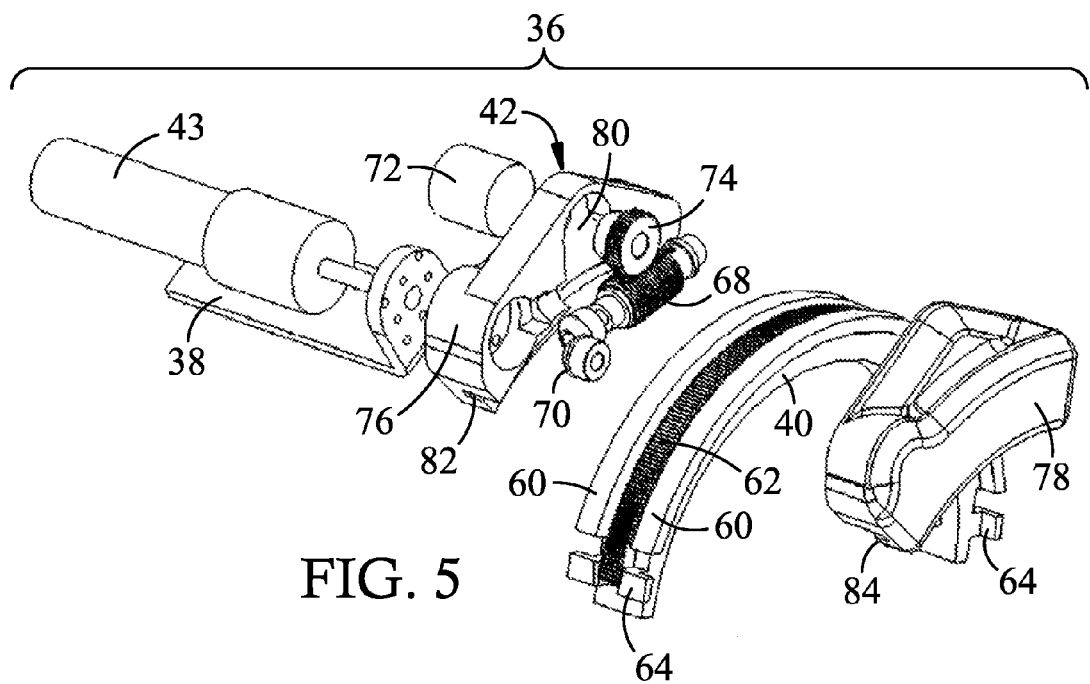
FIG. 5 is an exploded view of the portion of the arm orthosis shown in FIG. 4.

FIGS. 4 and 5 are perspective views of attachment mechanism 36 partially exposed and exploded, respectively. Attachment mechanism 36 generally includes translational mechanism 42 and arcuate member 40. Arcuate member 40 generally includes a pair of opposed bearing members 60 and a centrally located drive gear 62 along the arcuate extent of member 40 between bearing members 60. Arcuate member 40 further includes mounting means 64 to provide the adjustable mounting of elongated members 44, 46. Any suitable adjustable securing method may be used for the attachment with mounting means 64 located within respective slots 52 of elongated members 44, 46. This adjustable attachment enables the orthosis 32 and better fit different link arms and provide bodily attachment at a wearer's preferred location.

Translational mechanism 42 generally includes electric humeral motor 43 coupled to a worm gear 68 through a set of bevel gears 70. Worm gear 68 is adapted to engage drive gear 62. Further shown is a mechanical position indicator 72, such as a potentiometer which is coupled through a follower gear 74 to worm gear 68. In this manner, the revolutions of worm gear 68 and the rotation or translation of humeral member 40 can be measured by a control circuit.

Translational mechanism 42 further includes top housing 76 and bottom housing 78 which are equipped with various recesses, such as recess 82, to contain gears 68, 70 and 74. Housings 76, 78 further include arcuate channels 82, 84 which are adapted to engage bearing members 60 when housing 76 and 78 are assembled around humeral member 40. Both bearing members 60 and arcuate channels 82, 84 have bearing surfaces which interface with each other to provide support for the elbow assembly 34 through arcuate member 40 from attachment member 38 even during relative movement between arcuate member 40 and translational mechanism 42.

Figure 6:
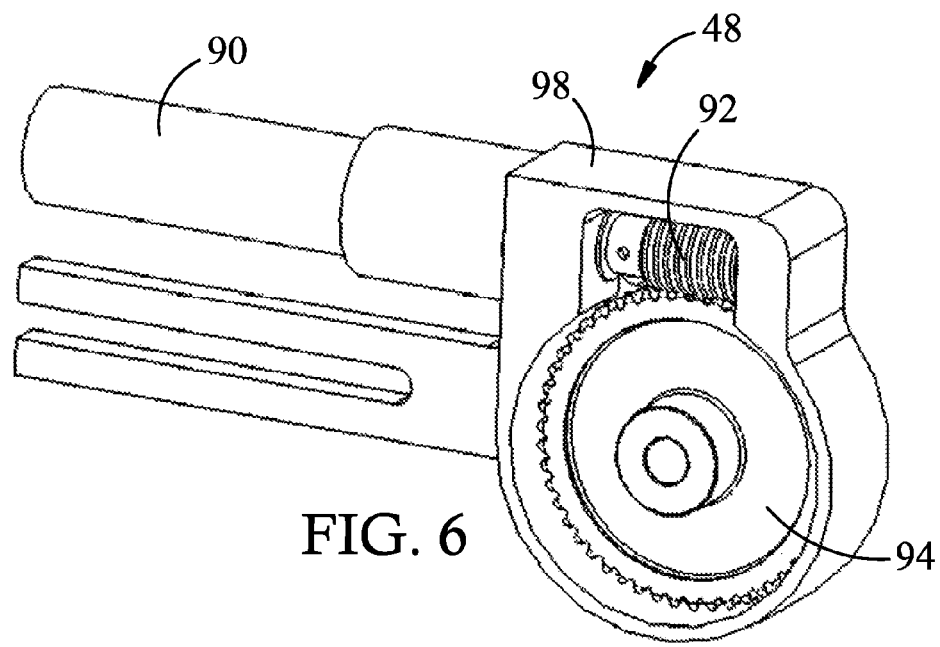
FIG. 6 is a perspective view of another portion of the arm orthosis of FIGS. 2 and 3.
Figure 7:
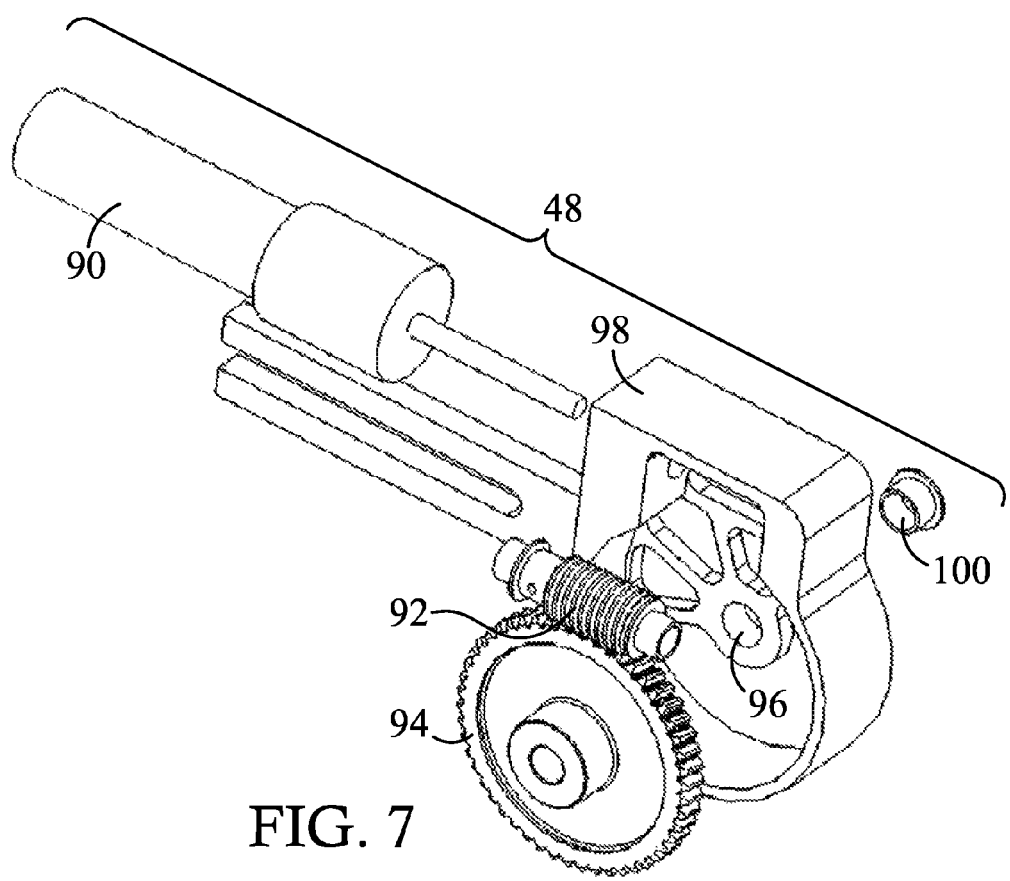
FIG. 7 is an exploded view of the components shown in FIG. 6.

FIGS. 6 and 7 show perspective views of flexion mechanism 48 in both an exposed and exploded mode, respectively. Flexion mechanism 48 generally includes electric motor 90, worm gear 92, drive gear 94 and a housing 98. Drive gear 94 is adapted for connection to an axle member 62 of FIG. 3 with its insertion through a pivotal point opening 96 in flexion mechanism housing 98 and further through a flange bearing 100 located in opening 96. In this manner rotation of the electric motor 90 causes worm gear 92 to rotate drive gear 94 and thereby cause rotation of forearm brace 50 with respect to elongated members 44, 46 (all of FIGS. 2 and 3).

Figure 13:
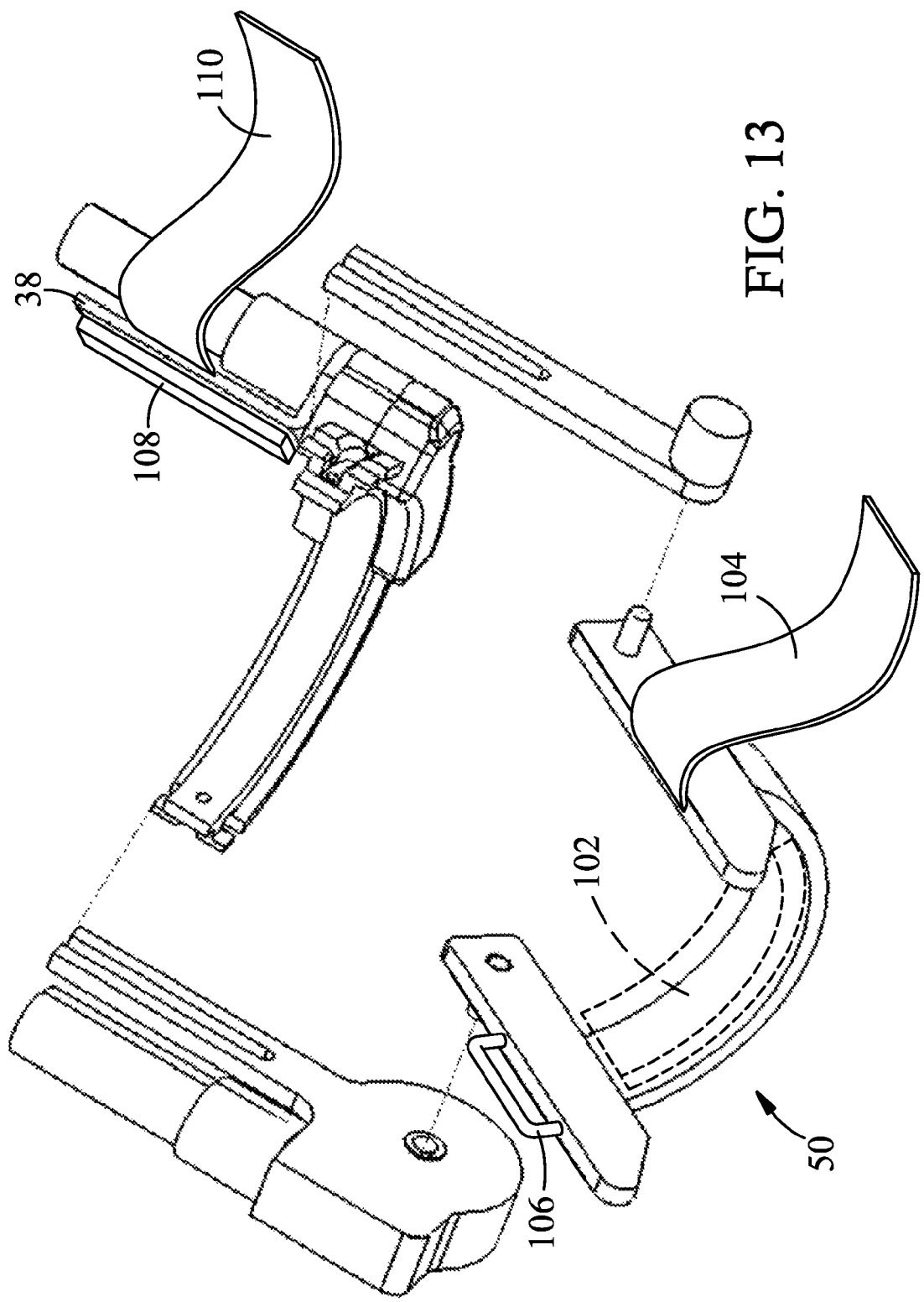
FIG. 13 shows a perspective view of the exploded arm orthosis of FIG. 3, further including means for attaching the orthosis to a patient.

FIG. 13 shows means for attaching forearm brace 50 to a human forearm and humeral arm attachment member 38 to a human upper arm. Forearm brace 50 shows the addition of padding 104, Velcro strap 106 and anchor ring 106. Typically, forearm brace 50 would be suitably sized to accommodate most, if not all forearms. Padding 102 may be specifically selected for each patient with an appropriate thickness and size to allow Velcro strap 104 to place appropriate pressure on the forearm when strap 104 is engaged with anchor ring 106. Likewise, attachment member 38 shows another pad 108 and another Velcro strap 110, and would include a similar anchor ring (not shown) on the back side to interface with Velcro strap 110.

Figure 8:
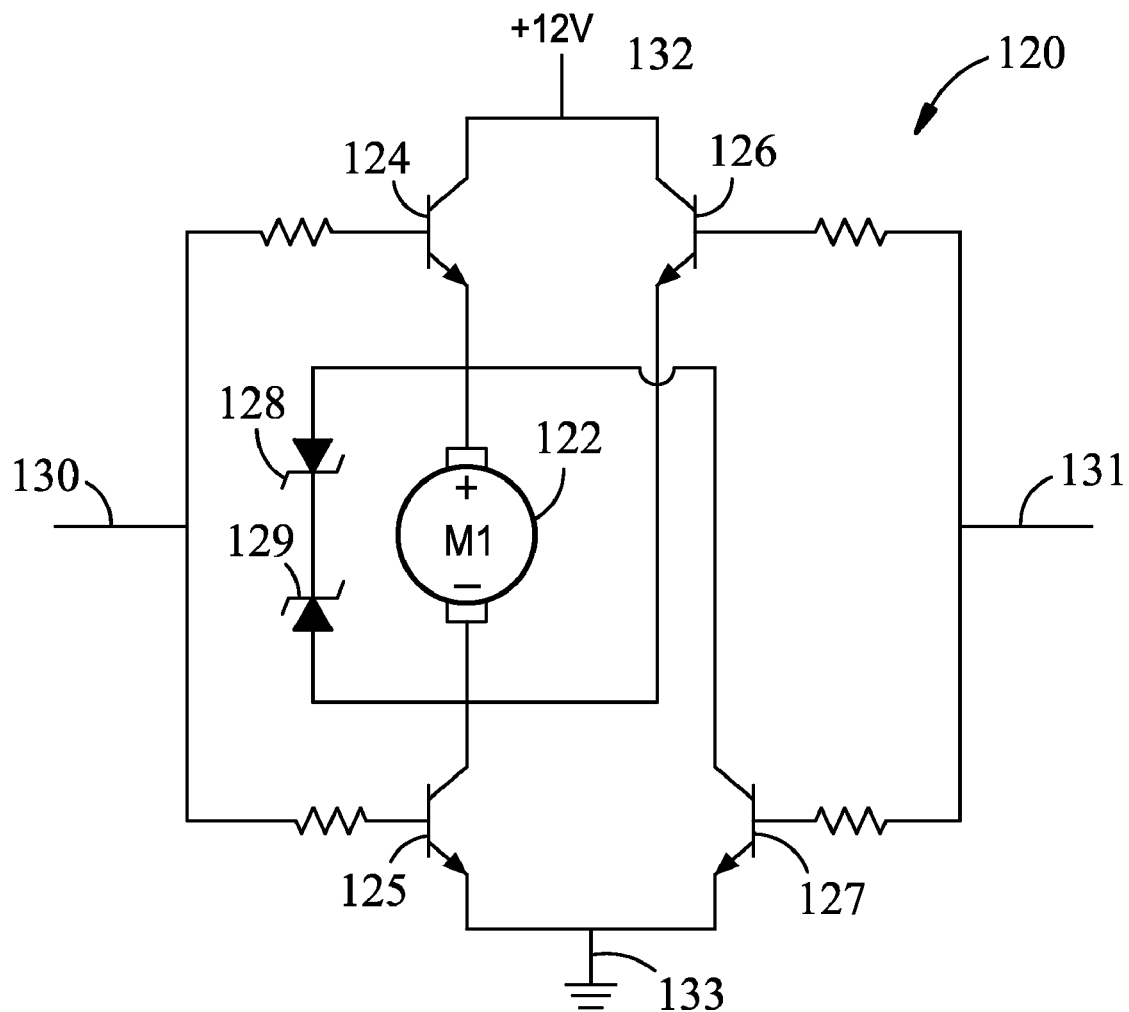
FIG. 8 is a circuit diagram of an H.-Bridge motor control circuit.

Translational mechanism 42 (FIGS. 2, 3, 4, 5) and flexion mechanism 48 (FIGS. 2, 3, 6, 7) include in their respective electric drive motors 43, 90, which are selected for orthosis 30 to achieve predetermined orthosis load and speed capacities with regard to their respective driven gear chains, as well as desirable weight and form limitations for use on orthosis 30. Drive control for motors 43, 90 is achieved through an H-Bridge circuit 120, depicted in FIG. 8, which is a classic method of controlling DC motors. It allows control with a minimum number of components and is available as a complete device. H-Bridge 120 offers three basic functions including rotate forward, rotate in reverse and stop, for a nominal motor 122. H-Bridge 120 commonly includes NPN transistors 124-127 and zener diodes 128, 129. Control is achieved by applying respective positive and ground voltages to input terminals 130, 131, with one polarity or the other. A positive voltage on input terminal 130 deactivates transistors 126, 127 and activates transistors 124, 125 to cause the positive voltage power supply 132 to be applied across motor 122, consistent with the polarity markings in FIG. 8, to drive motor 122 in a forward direction. A positive voltage on input terminal 131 deactivates transistors 124, 125 and activates transistors 126, 127 to cause the positive voltage power supply 132 to be applied across motor 122 with the opposite polarity to the markings shown in FIG. 8, to drive motor 122 in a reverse direction. A ground signal on input terminals 130, 131 deactivates all transistors 124-127 to cause motor 122 to stop. Motor speed control is provided by pulse width modulation of the voltage power supply applied across terminals 132, 133.

The H-bridge is available as a complete device on one chip, including a pair of H-Bridges capable of driving two separate motors. However, limitations to this arrangement include heat buildup in high current situations. Most H-bridge chips have limitations to current at values such as 0.5-1.0 A. In order to provide the necessary power for practical ergonomic efficiency of the present apparatus, separate drive components may be preferred to reduce the heat build-up resulting from simultaneous use.

Figure 9:
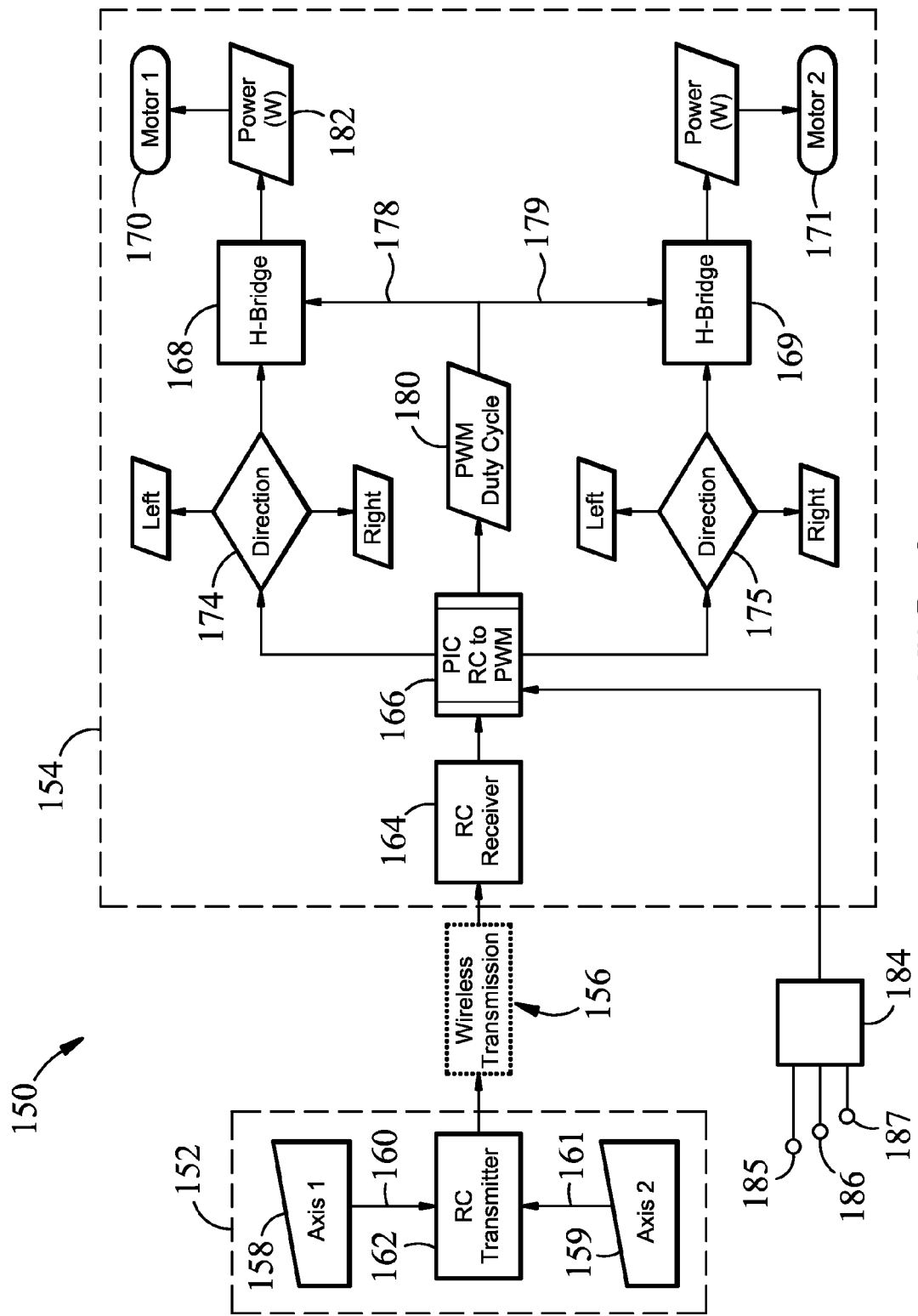
FIG. 9 is a functional block diagram of a control circuit suitable for use with embodiments of the present invention.
Figure 10:
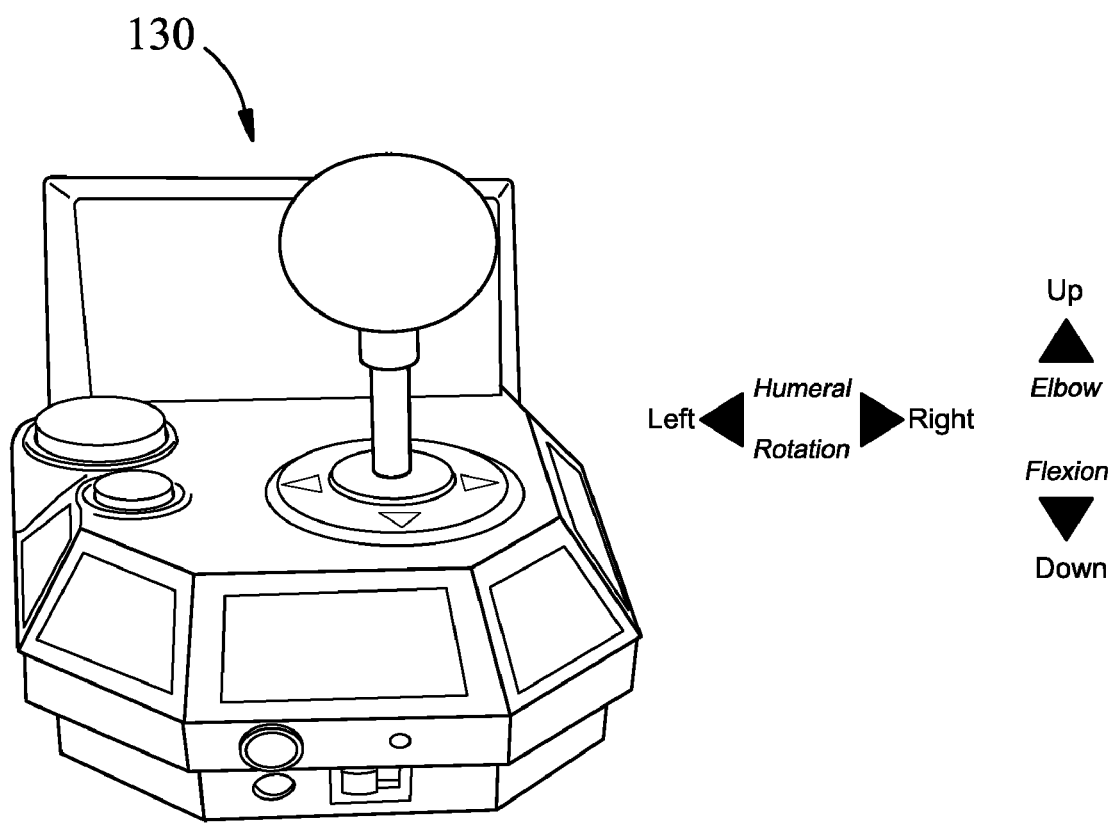
FIG. 10 is a perspective view of a joystick controller suitable for use with the control system of FIG. 9.

FIG. 9 shows a nominal control system 150 adapted for controlling an orthosis having two independent dimensions of movement. System 150 typically includes input circuitry 152 and motor control circuitry 154, along with a connection 156, which may be a wireless connection there between. Input circuitry 152 shows separate inputs 158, 159 for independent control of two dimensions of movement. Inputs 158, 159 may be readily embodied in a joystick controller, as shown in FIG. 10, selected to provide a separate continuously variable output signal 160, 161 responsive to joystick position in relation to each of the two orthogonal axes of movement thereof. These continuously variable input signals 160, 161 are transmitted to control circuitry 154 by any suitable connection 156, such as a radio control transmitter 162.

Control circuitry 154 includes a complimentary radio control receiver 164 adapted to receive and demodulate the continuously variable input signals 160, 161. Input signals 160, 161 are then coupled to a programmable integrated circuit or PIC 166 adapted to translate them to provide appropriate control signals for separate H-Bridge circuits 168, 169 adapted to control the independent dimensions of movement determined by motors 170, 171, respectively. More specifically, PIC 166 is adapted to provide direction control signals as represented by function blocks 174, 175 along with separate respective magnitude signals 178, 179 as represented by function block 180. Motor control signals from each H-Bridge circuit 168, 169 are coupled to respective power switching circuits 182, 183 for directly controlling power applied to respective motors 170, 171.

Continuously variable signals 160, 161 encode control information including desired direction and magnitude of movement and lack of movement for their respective dimensions of movement. Signals 160, 161 might nominally vary between one (1) volt and five (5) volts representing of the extreme positions of an axis of a joystick controller, with a value of 2.8 volts representing a neutral center position. This encoded control information needs to be translated from the continuously variable signals 160, 161 in two discrete directions, a magnitude and stop signals for use with respective H-Bridge circuits 168, 169.

Figure 11:
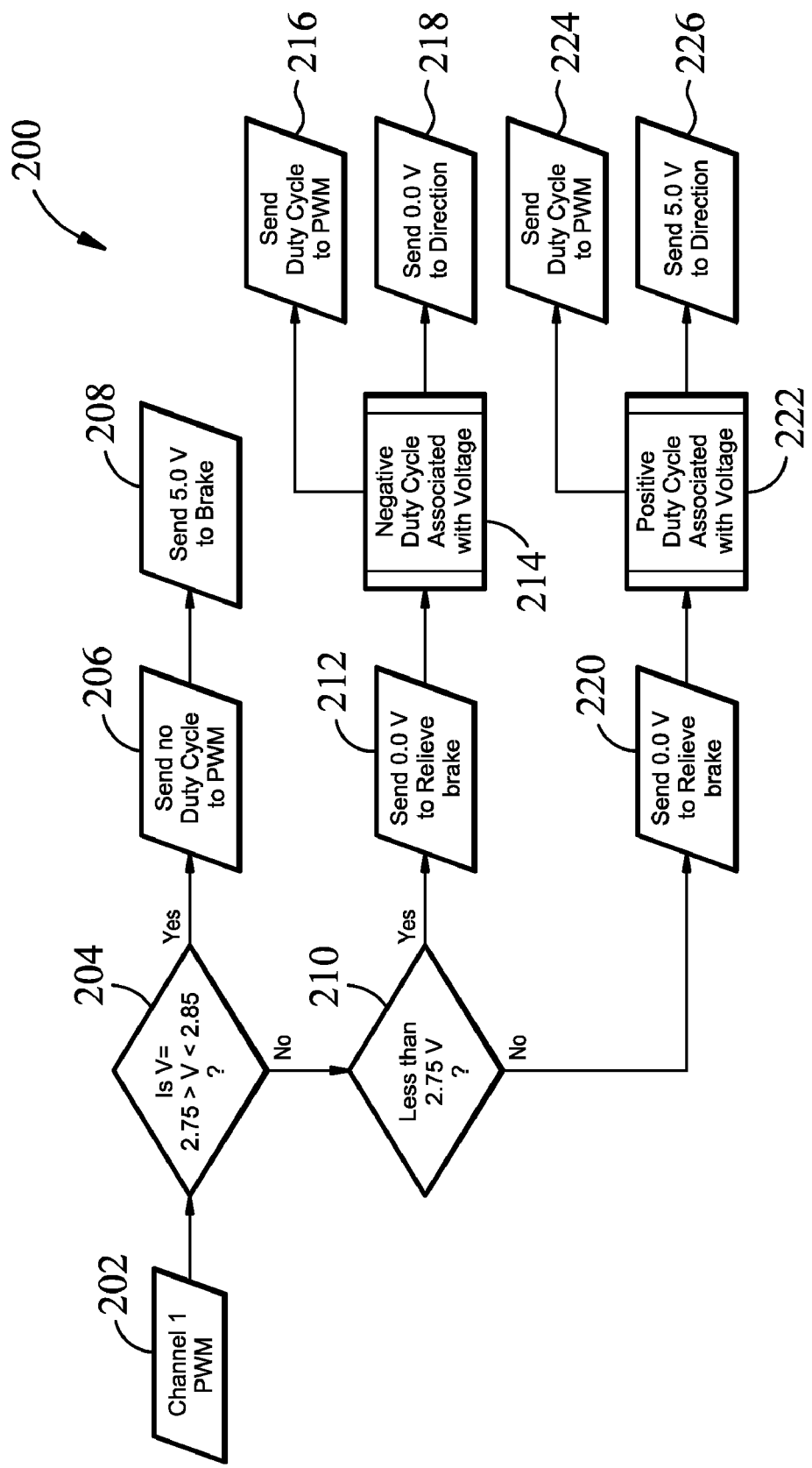
FIG. 11 is a logical block diagram of a portion of the system of FIG. 9.

The above translation is the function performed by PIC 166 as shown in the logic diagram 200 of FIG. 11. Logic diagram 200 is separately applicable to each of the input signals 160, 161, but is described herein only once. A wireless radio controlled transmitter 162 and receiver 164 (FIG. 9) typically transmits separate channels for two independent control signals, which separate channels are separated from each other in demodulation, converted to sampled digital signals and coupled to a separate channel 202 of logic diagram 200. A first decision block 204 determines if the nominal zero position voltage (2.8 volts) is present. If so, no duty cycle information is sent by function block 206 to the pulse width modulation controller 180 (FIG. 9), and a brake signal is sent to the respective H-Bridge by function block 208. If the nominal, zero position voltage is not detected another decision block 210 determines if the input voltage is in the lower voltage range, below the zero position voltage, or alternatively in the higher voltage range, above the zero position voltage, for use in determining the direction of desired movement indicated by the input signal. If the lower voltage range is detected by decision block 210, a brake release signal is provided by function block 212, and a further function block 214 determines the desired duty cycle represented by the input signal voltage for use by function block 216, as well as the direction control voltage for use by function block 218. If the higher voltage range is detected by decision block 210, a brake release signal is provided by function block 220, and a further function block 222 determines the desired duty cycle represented by the input signal voltage for use by function block 224, as well as the direction control voltage for use by function block 226.

FIG. 9 shows how the specifically formatted information generated by a joystick and transmitted by a radio control system may be interpreted and/or translated into the specific control signals used by H-Bridge circuits 168, 169. Likewise, various types of input signals may be accepted by control circuit 154 for use in controlling motors 170, 171. One interesting set of control signals are represented by input block 184 and generated by a multiplicity of myoelectric sensors 185-187.

A myoelectric signal, also called a motor action potential, is an electrical impulse that produces contraction of muscle fibers in the body. Myoelectric signals have frequencies ranging from a few hertz to about 300 Hz, and voltages ranging from approximately 10 microvolts to 1 millivolt. Myoelectric signals are detected by placing three electrodes on the skin. Two electrodes are positioned so there is a voltage between them when a myoelectric signal occurs. The third electrode is placed in a neutral area, and its output is used to cancel the noise that can otherwise interfere with the signals from the other two electrodes. The output voltage is processed using a differential amplifier. The output of this amplifier has much higher voltage than the myoelectric signals themselves. This higher voltage, which produces significant current, can be used to control electromechanical or electronic devices.

Thus, a user of the orthosis may be suitably wired to use specific muscle signals to operate the orthosis. The limited information signals produced from the sensors 185-187 and input block 184 may be processed in a manner similar to that described above to provide suitable motor control signals. This control aspect would be implemented with adequate safety features, such as the feedback function described below.

In order to further improve the functionality of control circuitry 154, it is desirable to incorporate a feedback function of motor position, representing the position of the orthosis in each dimension of movement, into the motor control function. Such a feedback function would protect the user from over driving of the orthosis. It was further determined that some users may not have the ability to use a full range of motion in either or both of the dimensions of movement of the orthosis, and that providing programmable limits on the range of motion could be a valuable addition to orthosis functionality. For this purpose, a simple mechanical position encoder or sensor was chosen based upon the simplicity of absolute motor position determination and the retained memory of motor position while the orthosis is not powered. Although simple, this absolute determination of motor position may still be used to provide adjustable or programmable limits for orthosis movement.

Figure 12:
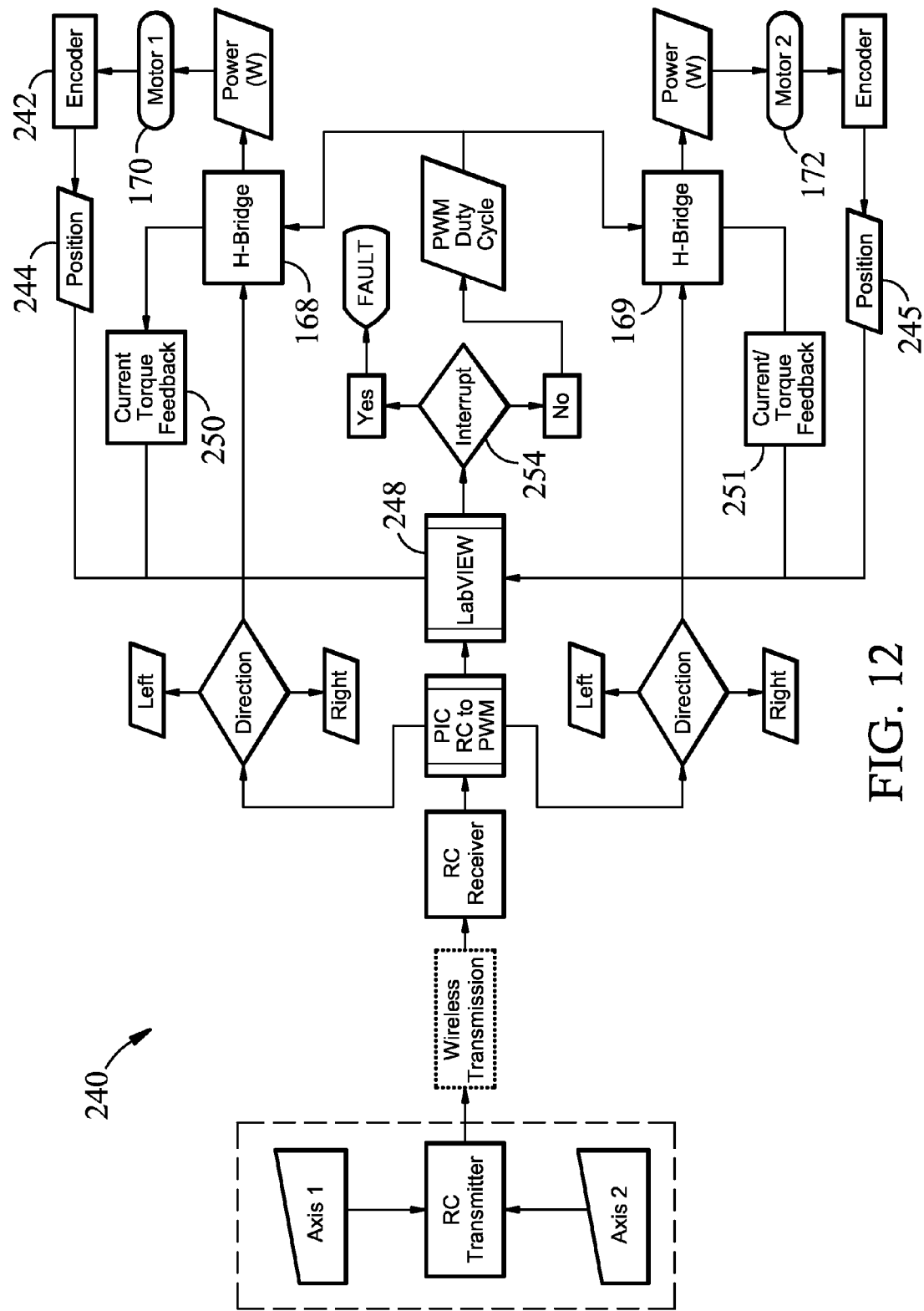
FIG. 12 is a functional block diagram of a control system suitable for use with embodiments of the present invention and further including a feedback function.

FIG. 12 shows a further functional block diagram 240 representing the feedback function of motor position as sensed by encoders 242, 243. The indications of encoders 242, 243 are sent by respective function blocks 244, 245 to a new feedback function control element 248. with the addition of feedback use in the control function, additional types of feedback information may be used such as current/torque feedback represented by respective blocks 250, 251. The results of using feedback control is that motors 170, 172 may have their power interrupted in the event of improper feedback data being sensed. This function is represented by decision block 254 which interrupts the pulse width modulation signal to the U-bridge circuits 168, 169 in the event of a fault indicated by the feedback data. Such a mechanical position sensor may also be applied directly to the orthosis in the manner of sensor 59 in FIGS. 2 and 3. In this case a separate input connection would be provided to control element 248.

The present invention is illustratively described above in reference to the disclosed embodiments. Various modifications and changes may be made to the disclosed embodiments by persons skilled in the art without departing from the scope of the present invention as defined in the appended claims.

The invention claimed is:

1. An arm orthosis adapted for providing humeral rotation and elbow flexion to a human arm, comprising:
    a humeral member adapted for attachment to an upper arm of a person;
    an elbow assembly adapted for attachment to a forearm of a person; and
    an attachment mechanism adapted to attach the elbow assembly to the humeral member and to effect rotation of the elbow assembly, in a manner of a human arm, with respect to the humeral member;
    wherein the elbow assembly includes a flexion mechanism for bending the elbow assembly in a manner of a human elbow; and
    wherein the attachment mechanism includes an arcuate member attached to the elbow assembly and a translational mechanism engaging the arcuate member and adapted to provide support to the arcuate member and translational movement of the arcuate member with respect to the translational mechanism to provide the rotation of the elbow assembly with respect to the humeral member.

2. The arm orthosis of claim 1 wherein the elbow assembly further includes a pair of elongated members individually and adjustably attached to opposing ends of the arcuate member.

3. The arm orthosis of claim 2, wherein the elbow assembly includes a forearm brace adapted for attachment to a forearm of a person, and including a pair of forearm brace axle sections adapted to individually, rotatably interface with a separate one of the pair of elongated members.

4. The arm orthosis of claim 3, further comprising a flexion drive attached to one of the elongated members and adapted to rotate the forearm brace with respect to one of the elongated members.

5. The arm orthosis of claim 4, wherein the flexion drive includes a drive gear affixed to one of the forearm brace axle sections at a point on that axle section which extends through an elongated member.

6. The arm orthosis of claim 5, wherein the flexion drive includes a flexion drive electrical motor and a worm gear located to engage the drive gear.

7. The arm orthosis of claim 6, wherein the flexion drive includes a flexion sensor adapted to indicate amounts of rotation between one elongated member and the forearm brace.

8. The arm orthosis of claim 7, wherein the flexion sensor includes a mechanical/electrical sensor coupled to sense amounts of rotation of the flexion drive electrical motor.

9. The arm orthosis of claim 2, wherein the pair of elongated members each includes a matching pivotal point adapted for location on either side of a human elbow of an aim attached to the orthosis.

10. The arm orthosis of claim 1, wherein the arcuate member includes an arcuate gear section located along the arcuate member, and further wherein the translational mechanism includes a worm gear and a humeral electric motor adapted to drive the arcuate gear section to cause the translational movement.

11. The arm orthosis of claim 10, wherein the translational mechanism includes a humeral sensor adapted to indicate amounts of movement between the arcuate member and the translational mechanism.

12. The arm orthosis of claim 11, wherein the humeral sensor includes a mechanical/electrical sensor coupled to sense amounts of rotation of the humeral electrical motor.

13. The arm orthosis of claim 1, wherein the attachment mechanism and the flexion mechanism are electrically driven, and further comprising a control system adapted for simultaneously and independently controlling driven movement of the attachment mechanism and the flexion mechanism.

14. The arm orthosis of claim 13, wherein the control system includes a joystick control adapted for providing one-handed simultaneous input signals for both the attachment mechanism and the flexion mechanism.

15. The arm orthosis of claim 14, wherein the joystick control is adapted to provide a variable magnitude input signal, and further wherein the control system is adapted to convert the variable magnitude input signal to a variable speed control for the electrically driven attachment mechanism and the flexion mechanism.

16. The arm orthosis of claim 13, wherein the control system includes control circuitry for the attachment mechanism and the flexion mechanism, a controller adapted for receiving user inputs and a wireless link between the controller and the control circuitry.

17. The arm orthosis of claim 13, wherein the control circuitry is adapted to receive feedback movement data from the attachment mechanism and the flexion mechanism and to limit drive signals to the attachment mechanism and the flexion mechanism in response to the feedback movement data.

18. The arm orthosis of claim 13, wherein the control system includes a logic controller for translating or interpreting inputs received from input circuitry, including myoelectric sensors.

19. The arm orthosis of claim 1, wherein the arcuate member includes upper and lower bearing surfaces arranged to enable supportive engagement of the arcuate member by the translational mechanism.

20. The arm orthosis of claim 1, wherein the humeral member is adapted for removable attachment to an upper aim of a person, and further wherein the elbow assembly is adapted for removable attachment to a forearm of a person.

* * * * *

UNITED STATES PATENT AND TRADEMARK OFFICE
CERTIFICATE OF CORRECTION

PATENT NO.       : 8,246,559 B2                                    Page 1 of 1
APPLICATION NO.  : 12/439555
DATED            : August 21, 2012
INVENTOR(S)      : Allen H. Hoffman et al.

It is certified that error appears in the above-identified patent and that said Letters Patent is hereby corrected as shown below:

In column 10, line 56 (claim 20), "upper aim" should read -- upper arm --

Signed and Sealed this
Sixth Day of November, 2012

David J. Kappos
*Director of the United States Patent and Trademark Office*